United States Patent
Matalgah

(10) Patent No.: US 9,454,887 B1
(45) Date of Patent: Sep. 27, 2016

(54) DOZE ALERT

(71) Applicant: Mustafa Q. Matalgah, Fort Worth, TX (US)

(72) Inventor: Mustafa Q. Matalgah, Fort Worth, TX (US)

(*) Notice: Subject to any disclaimer, the term of this patent is extended or adjusted under 35 U.S.C. 154(b) by 0 days.

(21) Appl. No.: 14/547,528

(22) Filed: Nov. 19, 2014

Related U.S. Application Data

(60) Provisional application No. 61/906,090, filed on Nov. 19, 2013.

(51) Int. Cl.
| | |
|---|---|
| *G08B 23/00* | (2006.01) |
| *G08B 21/06* | (2006.01) |
| *B60K 28/06* | (2006.01) |
| *A61B 5/00* | (2006.01) |
| *G08B 21/04* | (2006.01) |

(52) U.S. Cl.
CPC ............ *G08B 21/06* (2013.01); *A61B 5/4809* (2013.01); *B60K 28/06* (2013.01); *G08B 21/0453* (2013.01); *G08B 23/00* (2013.01)

(58) Field of Classification Search
CPC .... G08B 21/06; G08B 28/06; A61B 5/0476; A61B 5/0022; A61B 5/6814; A61B 5/7455; A61B 5/18; A61B 5/0006; A61B 5/7405; A61B 5/6803; A61B 5/4812; A61B 5/4809; A61M 21/00; A61M 2205/3375; A61M 2021/0027; H04R 2499/13; H04R 3/00; B60R 16/0236; B60R 21/01552; B60K 28/06

USPC ............ 340/575, 576, 573.1, 573.7, 439; 600/544, 545, 538, 595

See application file for complete search history.

(56) References Cited

U.S. PATENT DOCUMENTS

| | | |
|---|---|---|
| 3,954,100 A | 5/1976 | Sem-Jacobsen |
| 7,027,621 B1 | 4/2006 | Prokoski |
| 7,427,924 B2 | 9/2008 | Ferrone et al. |
| RE41,376 E | 6/2010 | Torch |
| 8,698,639 B2 | 4/2014 | Fung et al. |
| 2009/0273478 A1 | 11/2009 | Mei |
| 2010/0076273 A1* | 3/2010 | Shigetou ................ G08B 21/06 600/300 |
| 2012/0212345 A1 | 8/2012 | Harman |
| 2012/0319869 A1* | 12/2012 | Dorfmann ............ G08B 21/06 340/945 |
| 2013/0159041 A1* | 6/2013 | Jayaraman ............... A61B 5/18 705/7.15 |
| 2013/0204153 A1* | 8/2013 | Buzhardt ............. A61B 5/0476 600/544 |
| 2013/0207804 A1* | 8/2013 | Li ......................... G08B 21/06 340/575 |
| 2014/0266739 A1 | 9/2014 | Chen |

* cited by examiner

*Primary Examiner* — Anh V La
(74) *Attorney, Agent, or Firm* — Kenneth L Tolar

(57) ABSTRACT

A doze alert includes a head cover having a plurality of EEG sensors mounted thereon for measuring brainwave activity. The sensors are in communication with a wireless transceiver that transmits the measurements to a monitoring station. If a majority of the measurements are below an acceptable threshold, the monitoring station generates a brightly colored message on a display screen and engages an audible alarm.

6 Claims, 2 Drawing Sheets

DOZE ALERT

CROSS REFERENCE TO RELATED APPLICATIONS

This application is entitled to the benefit of provisional patent application No. 61/906,090 filed on Nov. 19, 2013, the specification of which is incorporated herein by reference.

BACKGROUND OF THE INVENTION

The present invention relates to a head cover that activates audible and visual alarms whenever the wearer is drowsy or dozing.

DESCRIPTION OF THE PRIOR ART

Numerous accidents occur each year due to people driving, operating heavy equipment and performing other dangerous tasks while fatigued. Though coffee, energy drinks and other over-the-counter products can prevent drowsiness, the effective duration of such products is limited. Furthermore, a person who consumes such products may fall asleep anyway and cause a severe accident. Accordingly, there is currently a need for a device that awakens or startles a person who is in danger of falling asleep during certain activities.

A review of the prior art reveals a few devices that are purportedly designed to prevent a person from dozing during certain activities. For example, U.S. Pat. No. 3,954,100 issued to Sem-Jacobsen discloses a flexible pad having EKG sensors therein for activating an alarm if a pilot or patient loses consciousness.

U.S. Pat. No. 7,427,924 to Ferrone discloses a system and method for monitoring driver fatigue including a steering wheel sensor that activates an alarm if the steering wheel moves irregularly, indicating driver fatigue.

U.S. published patent application no. 2009/0273478 to Mei discloses a sleep alert wristband including a pulse sensor for activating an alarm when a wearer begins dozing.

U.S. published patent application no. 2012/0212345 to Harman discloses an earpiece having various sensors that monitor eyelid movement to determine if a wearer is drowsy.

U.S. published U.S. Pat. No. 7,027,621 issued to Prokoski discloses an infrared camera for capturing images of a person's head and face to determine impairment.

U.S. Pat. No. RE41376 to Torch discloses a drowsiness monitor including a head frame having light emitters and sensors thereon for detecting whether the wearer's eyelids are closed.

As indicated above, most of the prior art devices employ pulse or eyelid sensors to monitor drowsiness. However, none of the above-referenced devices employ an EEG to monitor brain activity. Billions of neutrons in the human brain produce an electrical charge as ions are pumped across their membranes. The ion exchange phenomenon occurs continuously as the ions are forced out of the neurons in phase with other ions to form small electrical waves of energy. The waves have a high amplitude during increased brain activity and a lower amplitude as brain activity decreases. The electrical potential generated by a single neuron is too small to be detected by a single EEG sensor. However, if multiple, high-gain sensors are aggregated, the signals emanating therefrom can be monitored to measure relative brain activity.

The present invention uses the above-described phenomenon by incorporating a plurality of EEG sensors into a head cover that wirelessly communicate with a remote computer to graphically display brainwave data. If brainwave activity is determined to be below a predetermined baseline, a series of alarms are initiated.

SUMMARY OF THE INVENTION

The present invention relates to a doze alert comprising a head cover having a plurality of EEG sensors mounted thereon for measuring brainwave activity. The sensors are in communication with a wireless transceiver that transmits the measurements to a monitoring station. If a majority of the measurements are below an acceptable, predetermined baseline, the monitoring station generates a brightly colored message on a display screen and engages an audible alarm.

It is therefore an object of the present invention to provide a head cover that emits an alert when a wearer is drowsy or dozing.

It is another object of the present invention to provide a doze alert that enhances the safety associated with operating a vehicle or other dangerous equipment.

Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
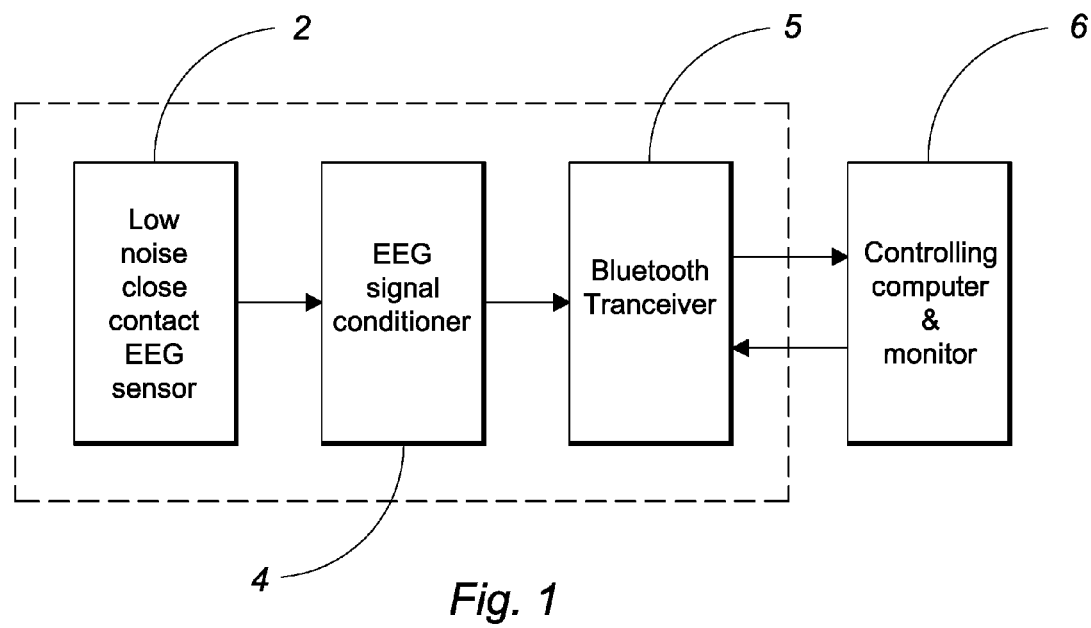
FIG. 1 is a block diagram of the major components of the doze alert according to the present invention.
Figure 2:
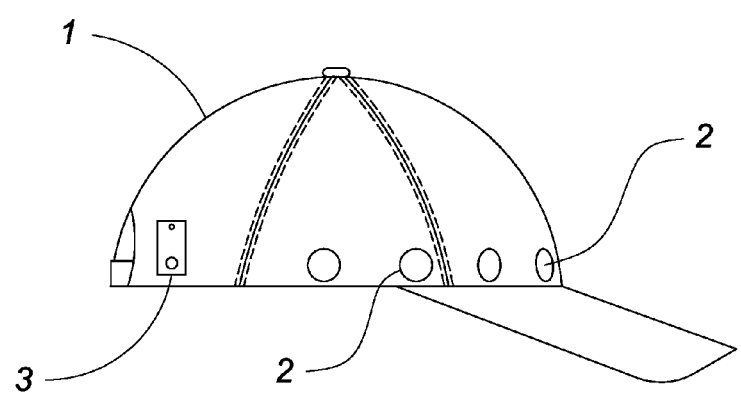
FIG. 2 is an isolated view of the head cover.
Figure 3:
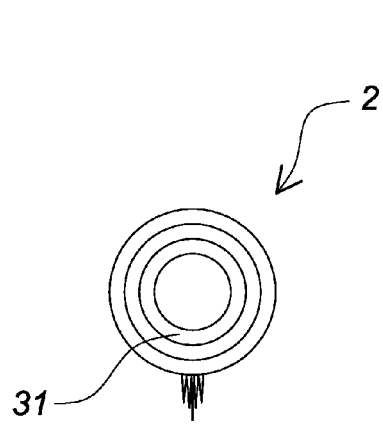
FIG. 3 is an isolated view of an exemplary sensor.
Figure 4:
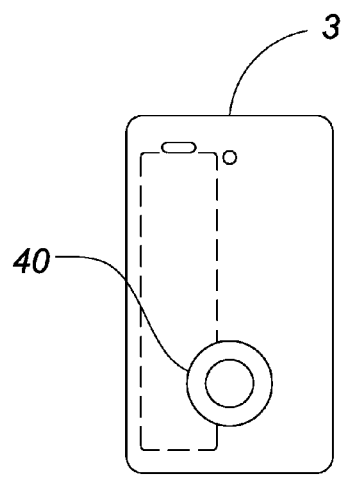
FIG. 4 is an isolated view of the communications module.
Figure 5:
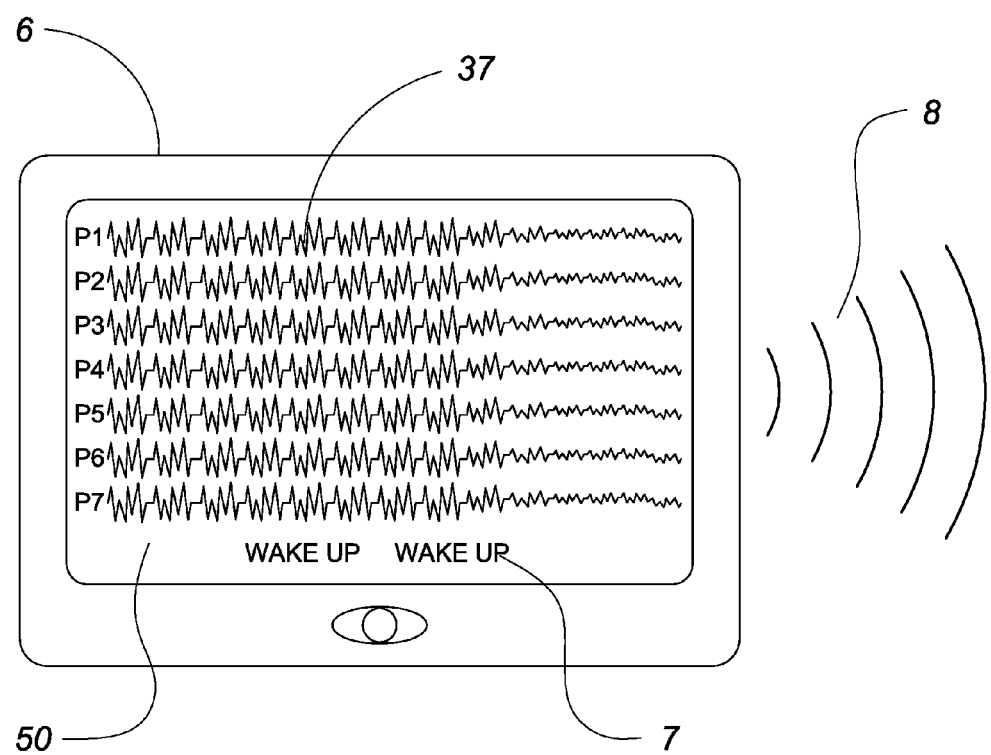
FIG. 5 is an isolated view of an exemplary monitor, i.e., a tablet computer.

The present invention relates to a doze alert comprising a head cover 1, such as a cap, hat, headband or headset, having at least a peripheral portion that rests on a wearer's scalp. Mounted on the peripheral portion are a plurality of high-gain EEG sensors 2 that engage the scalp whenever the head cover is worn to measure brainwave activity. The sensors each include a spirally wound antenna 31 that is positioned proximal a side of the sensor that will contact a wearer's skin. The antenna is designed to intercept 0.5 to 5 Hz waveforms, which are amplified by the electronics.

The sensors are connected to a communications module 3 mounted on the headgear that includes a signal conditioner 4 and a wireless transceiver 5. The conditioner filters and aggregates the brainwave signals from each of the sensors to form a combined output signal that is delivered to the transceiver. However, the conditioner assigns a unique identifier to each sensor signal as the combined signal is delivered to the transceiver. The transceiver uses conventional wireless-communication technology, such as that commonly marketed and sold under the trademark Bluetooth®. A power button 40 allows a user to disable the device when not needed.

The doze alert also includes a monitoring station 6, such as a desktop or laptop computer, a smart phone, a tablet computer or any other similar processor having wireless-communication capabilities. The monitor includes software that analyzes the combined output signal from the transceiver and separately deciphers each sensor's signal according to the assigned identifier. Thus, the software separately analyzes the brainwave data from each sensor, and generates an individual plot 37 of each sensor signal on a display screen 50. The software also compares the amplitude of each sensor's signal with a baseline amplitude as determined by measuring the wearer's brainwave activity while fully alert. If the amplitude of the signal from a majority of the sensors, for example 4/7, is less than half of the baseline amplitude, the software generates a brightly colored message 7 on the screen and engages an audible alarm 8. Once the measured signals return to a normal range, the audible and visual alarms are disabled.

The above-described device is not limited to the exact details of construction and enumeration of parts provided herein. For example, though the device has been primarily depicted and described as a doze alert, it can also be configured to monitor certain medical parameters, such as blood sugar, pulse, blood pressure, or any similar variable, and activate an appropriate alarm on the monitoring station if any such parameter is outside an acceptable range. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A doze alert comprising:

a head cover having at least a peripheral portion that rests on a wearer's scalp;

a plurality of EEG sensors mounted on the peripheral portion of said head cover that engage the scalp whenever the head cover is worn to measure brainwave signals, wherein said sensors are connected to a communications module mounted on the head cover, said communications module including a wireless transceiver and a signal conditioner that filters and aggregates brainwave signals from said sensors to form a combined output signal that is delivered to the transceiver;

a remote monitor in wireless communication with the wireless transceiver and said sensors, said monitor having a display screen that graphically depicts brain waves that are measured by each of said sensors, said remote monitor having an alarm means for alerting the wearer when the brain waves measured by said sensors is below a preestablished threshold.

2. The doze alert according to claim 1 wherein said monitor includes a processor that analyzes the combined output signal and identifies a contribution to the combined output signal from each of said sensors to allow said monitor to separately depict on said display screen the brain waves that are measured by each of said sensors.

3. The doze alert according to claim 2 wherein said processor compares an amplitude of the brave waves measured by each of said sensors with a baseline amplitude corresponding to a wearer's brainwave activity when fully alert.

4. The doze alert according to claim 3 wherein said alarm means comprises said processor generating a brightly colored message that is depicted on said display screen only when the amplitude of the brain waves measured by a majority of the sensors is less than half of the baseline amplitude.

5. The doze alert according to claim 4 wherein said alarm means comprises said processor generating an audible alarm only when the amplitude of the brain waves measured by a majority of the sensors is less than half of the baseline amplitude.

6. The doze alert according to claim 5 wherein each of said sensors includes a spirally wound antenna that is positioned proximal a side of the sensors that will contact a wearer's skin.

\* \* \* \* \*